(12) United States Patent
Scott

(10) Patent No.: US 7,125,392 B2
(45) Date of Patent: Oct. 24, 2006

(54) ANKLE-FOOT ORTHOTIC DEVICE AND METHOD

(75) Inventor: Kyle R. Scott, Salem, OR (US)

(73) Assignee: Oregon Orthotic System, Inc., Albany, OR (US)

( * ) Notice: Subject to any disclaimer, the term of this patent is extended or adjusted under 35 U.S.C. 154(b) by 0 days.

(21) Appl. No.: 10/642,046

(22) Filed: Aug. 15, 2003

(65) Prior Publication Data
US 2005/0038365 A1 Feb. 17, 2005

(51) Int. Cl.
*A61F 5/00* (2006.01)
*A61F 5/37* (2006.01)

(52) U.S. Cl. ............................ 602/23; 602/28; 128/882

(58) Field of Classification Search ............... None
See application file for complete search history.

(56) References Cited

U.S. PATENT DOCUMENTS

| | | | | |
|---|---|---|---|---|
| 2,584,010 A | * | 1/1952 | Goffredo | 602/28 |
| 3,504,668 A | * | 4/1970 | Boudon | 602/28 |
| 3,783,534 A | * | 1/1974 | Phillips et al. | 36/72 R |
| 3,916,886 A | | 11/1975 | Rogers | |
| 3,948,253 A | * | 4/1976 | Burke | 602/29 |
| 3,986,501 A | | 10/1976 | Schad | |
| 4,136,404 A | * | 1/1979 | Lange | 2/22 |
| 4,329,982 A | | 5/1982 | Heaney | 602/28 |
| 4,534,122 A | * | 8/1985 | MacPhail | 36/88 |
| 4,550,721 A | * | 11/1985 | Michel | 602/27 |
| 4,559,934 A | * | 12/1985 | Philipp | 602/27 |
| 4,692,946 A | * | 9/1987 | Jurga | 2/22 |
| 4,876,745 A | * | 10/1989 | Richards | 2/24 |
| 5,020,523 A | | 6/1991 | Bodine | |
| 5,112,296 A | * | 5/1992 | Beard et al. | 602/28 |
| 5,219,324 A | | 6/1993 | Hall | |
| 5,277,699 A | * | 1/1994 | Williamson | 602/28 |
| 5,370,604 A | | 12/1994 | Bernardoni | |
| 5,573,501 A | | 11/1996 | Ruscito et al. | |
| 5,605,535 A | | 2/1997 | Lepage | |
| 5,609,568 A | | 3/1997 | Andrews | |
| 5,665,059 A | | 9/1997 | Klearman et al. | |
| 5,697,893 A | * | 12/1997 | Rhenter | 602/27 |
| 5,732,411 A | * | 3/1998 | Coleman et al. | 2/22 |
| 5,776,090 A | | 7/1998 | Bergmann et al. | |
| 5,799,659 A | | 9/1998 | Stano | |
| 5,817,041 A | | 10/1998 | Bader | |
| 5,857,987 A | * | 1/1999 | Habermeyer | 602/23 |
| 5,887,591 A | | 3/1999 | Powell et al. | |
| 5,897,515 A | | 4/1999 | Willner et al. | |
| 5,897,520 A | | 4/1999 | Gerig | |
| 5,898,939 A | * | 5/1999 | Schramm | 2/22 |
| 5,961,477 A | | 10/1999 | Turtzko | |
| 6,019,741 A | | 2/2000 | Prieskorn | |
| 6,146,344 A | | 11/2000 | Bader | |
| 6,146,349 A | | 11/2000 | Rothschild et al. | |

(Continued)

Primary Examiner—Henry Bennett
Assistant Examiner—Karl Petrik
(74) Attorney, Agent, or Firm—Ryhdak & Suri LLP

(57) ABSTRACT

Provided is an ankle-foot orthotic device and method for preventing foot drop of a person wearing footwear. The device includes an elongated member adapted to extend along an anterior portion of the lower leg and conforms to a portion of the dorsal surface of the foot. The elongated member is further adapted to secure to an upper outer region of the person's footwear. Securing the device to the lower leg and footwear of a person maintains the foot in a dorsiflexion position. The elongated member may include an upper portion positionable relative to an intermediate portion providing an ankle-foot orthotic device variable in length.

14 Claims, 3 Drawing Sheets

U.S. PATENT DOCUMENTS

| | | |
|---|---|---|
| 6,319,218 B1 | 11/2001 | Birmingham |
| 6,361,517 B1 * | 3/2002 | Slinger ........................ 602/28 |
| 6,727,682 B1 * | 4/2004 | Tobin ..................... 324/117 R |
| 6,827,696 B1 * | 12/2004 | Maguire ..................... 602/27 |
| 2002/0188238 A1 | 12/2002 | Townsend et al. |
| 2004/0102727 A1 * | 5/2004 | Smits ......................... 602/28 |
| 2004/0134500 A1 * | 7/2004 | Ingimundarson et al. ... 128/882 |

* cited by examiner

Fig. 1
Fig. 2
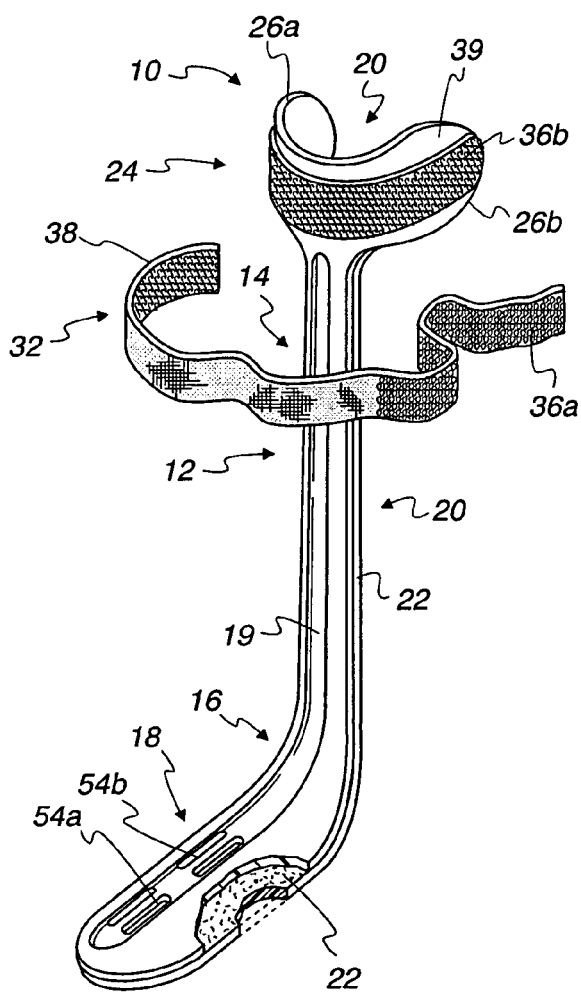
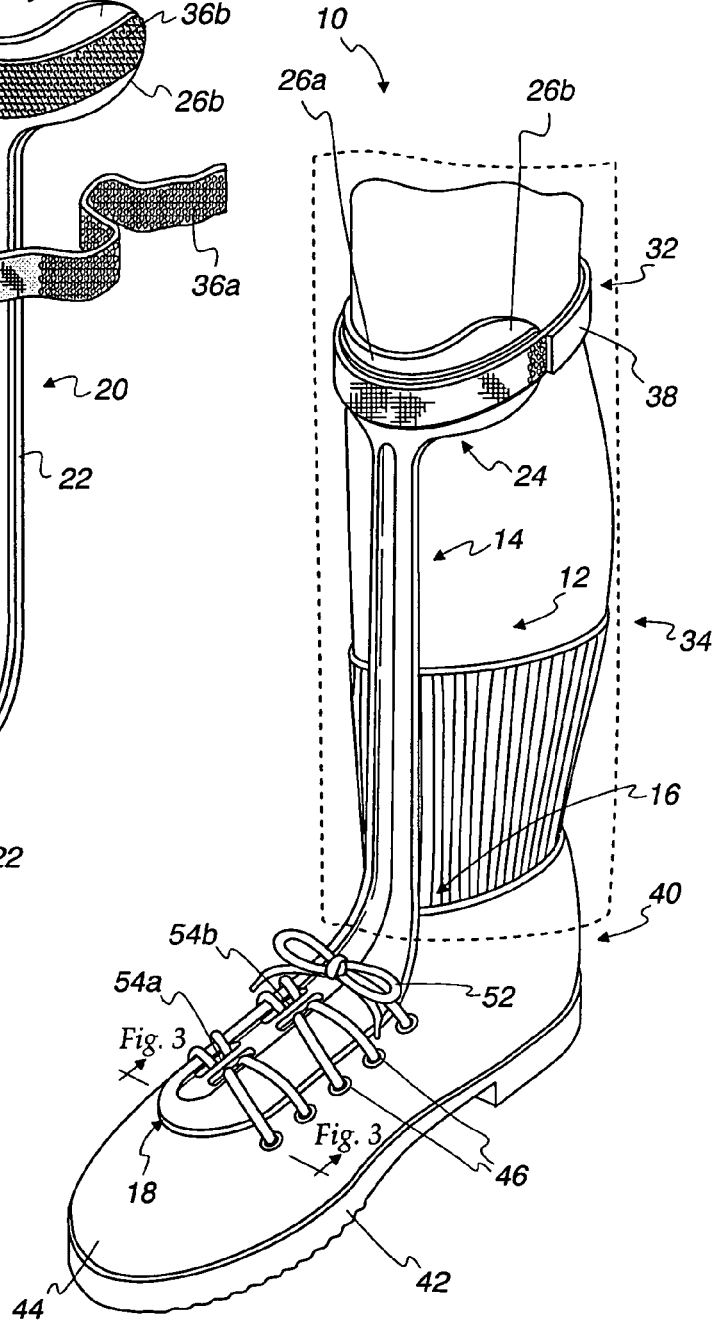

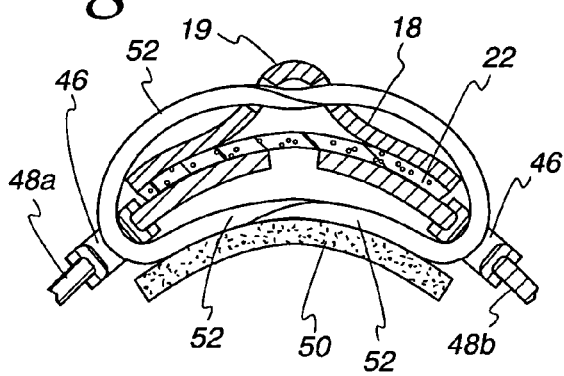
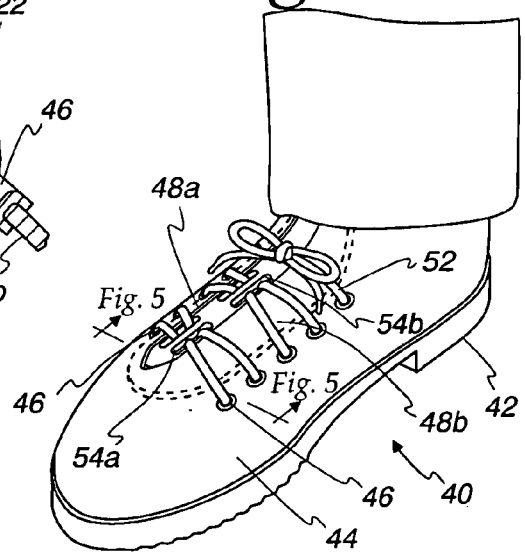
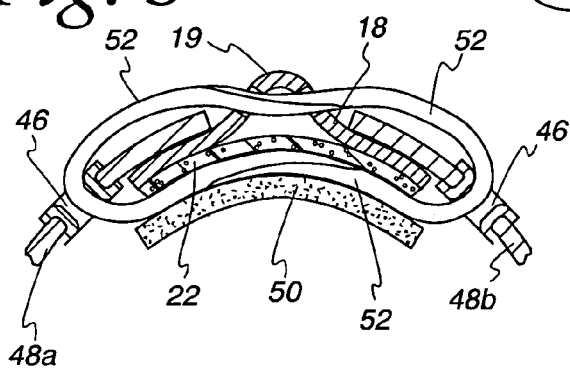
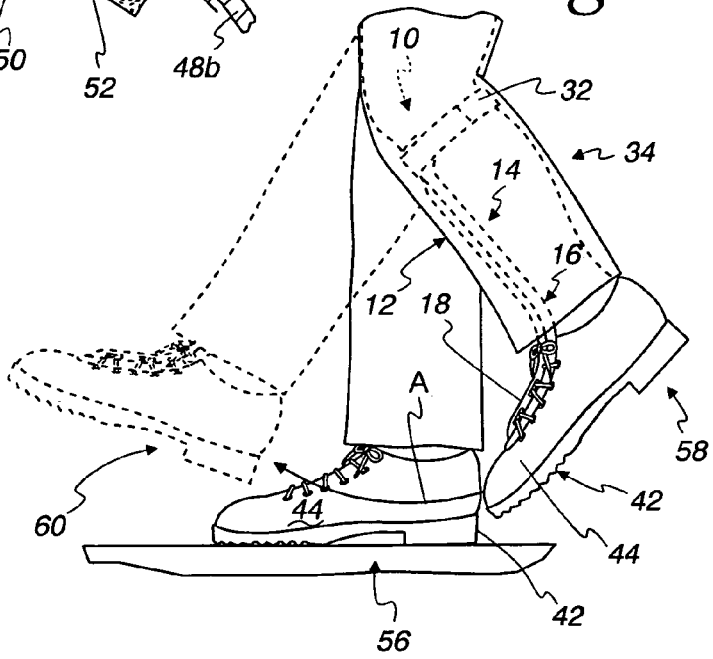

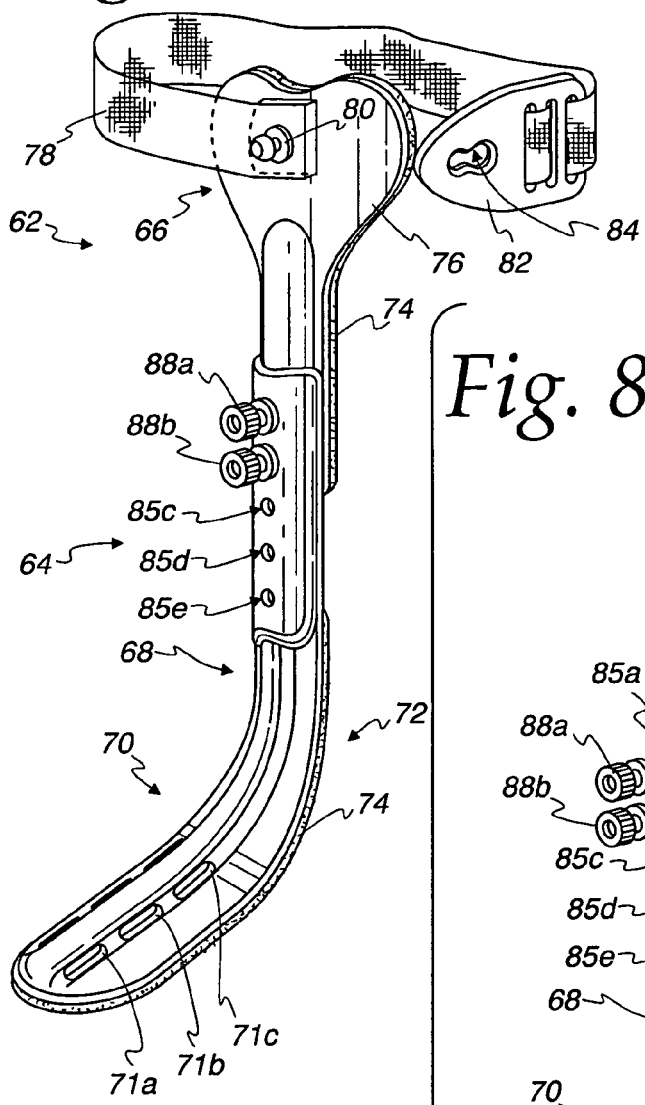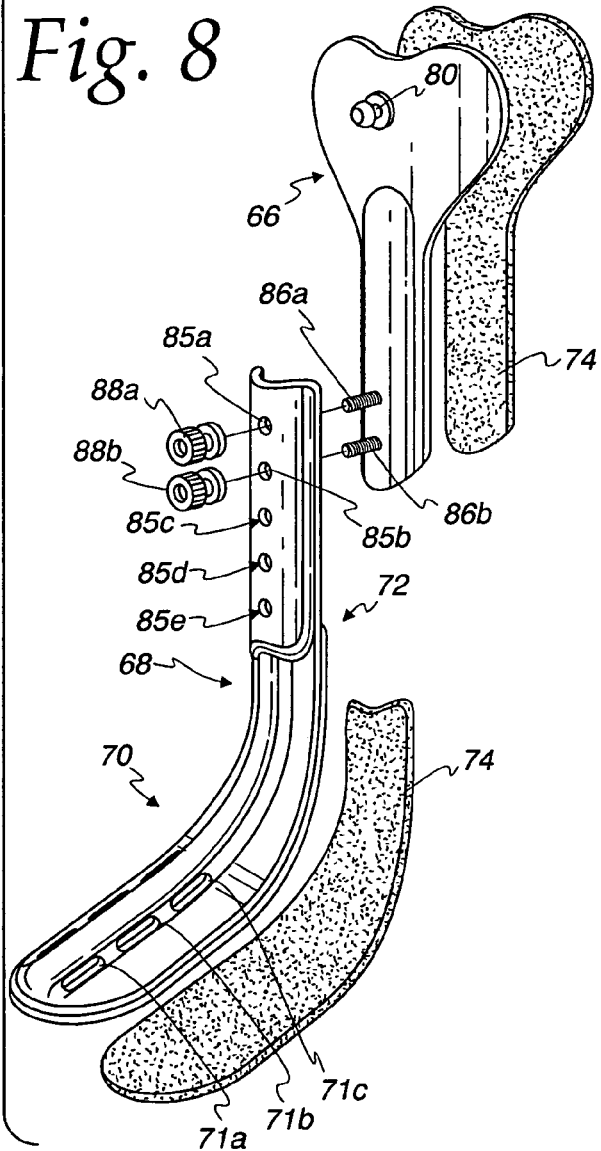

019# ANKLE-FOOT ORTHOTIC DEVICE AND METHOD

FIELD OF THE INVENTION

The present invention relates generally to an ankle-foot orthosis and in particular to an anterior ankle-foot orthosis for treatment of foot drop.

BACKGROUND OF THE INVENTION

Foot drop is a condition whereby movement and control of the ankle is reduced due to weakened dorsiflexion muscles. Foot drop may be the result of a neurological, muscular, or anatomical disorder or injury. This disorder impairs normal ambulation as the dorsiflexion muscles are unable to support the foot during swing and heel strike. Left untreated, the diminished dorsiflexion control increases the risk of falling or further foot injury. In addition, a person with foot drop may strain or damage other joints such as the knee or hip, as the person attempts to compensate for the foot drop impediment during ambulation.

Orthotic treatments for foot drop typically isolate or immobilize the ankle giving the patient more control and stability during the gait cycle. Conventional lower leg orthoses, however, are cumbersome, bulky, and difficult to wear with ordinary footwear. Devices insertable into footwear tend to cause discomfort and impart excessive pressure on the wearer's foot and leg. In addition, prolonged wear tends to cause undesirable friction between the device and the wearer's skin resulting in pain and tissue trauma.

A need exists for an orthotic device to treat foot drop that is easy to apply and provides comfort to the wearer particularly during periods of prolonged wear. A need further exists for a lower leg orthotic device that is readily attachable to the exterior of standard footwear and can accommodate lower legs having various lengths.

SUMMARY OF THE INVENTION

In accordance with the present invention, an ankle-foot orthotic device is provided that is securable to a lower leg of a person wearing footwear, which can be a shoe, for example, to prevent foot drop. The device includes an elongated member having an upper portion, typically an intermediate portion, a lower portion, a suitable structure for securing the lower portion to an upper region of the wearer's footwear, and a securing member for securing the upper portion to the lower leg.

The upper portion is adapted to extend along an anterior portion of the lower leg below the person's knee. The lower portion generally conforms to a portion of the dorsal surface of the foot and is adapted to engage an upper outer region of the footwear. The intermediate portion extends between the upper portion and the lower portion. The intermediate portion transitions from the upper to lower portions and can be considered to be part of either the upper and lower portions of the orthotic device, which upper and lower portions can be formed as a single integral member. The lower portion is securable to an upper region of the wearer's footwear and the securing member secures the upper portion to the lower leg.

When the inventive device is applied to a person's lower leg and footwear as intended, the device maintains the person's foot in a dorsiflexion position preventing foot drop during toe-off and/or leg swing and preventing foot slap during leg swing and/or heel strike. This enables the person experiencing foot drop to walk or otherwise ambulate with a normal gait and reduces the risk of further injury or strain to the impaired foot, other limbs and joints as a result of utilizing the present invention.

In one embodiment of the present invention, the lower portion of the inventive orthosis is adapted to engage an outer portion of the wearer's footwear. Consequently, the orthosis is configured so that it is not inserted into or in the interior portion of the shoe or footwear where the wearer's foot is placed. Thus, the orthosis does not contact the wearer's foot. The lower portion includes at least one opening or slot permitting shoelaces of the footwear to pass through the opening or slot to permit the orthosis to be more securely affixed to the footwear. The shoelaces may then be tied or laced in any conventional manner to secure the lower portion to the footwear and concomitantly secure the footwear to the wearer's foot. The elongated member may also include a reinforcing rib that extends longitudinally along a generally central region of the elongated member. The reinforcing rib provides added rigidity to the elongated member.

In an alternate embodiment of the present invention, the lower portion is adapted to be insertable between an upper region and a tongue of the footwear and outside the interior of the footwear with the person's foot being located in the interior portion of the footwear. The lower portion of the orthosis may be either narrower or wider in width than the intermediate portion as desired in order to fit between the upper region of the footwear and the tongue.

The lower portion of the orthosis typically includes at least one opening or slot enabling shoelaces to pass through the opening or slot thereby securing the lower portion to the footwear. Alternatively, the lower portion may have no opening and be adapted to friction-fit within footwear having a cavity formed between the upper region of the footwear and the tongue.

One advantage of the present invention is that none of the orthosis, and in particular the lower portion, is in direct contact with the wearer's foot. This reduces the possibility of skin irritation or tissue damage to the person wearing the device, particularly during periods of prolonged wear, and increases the wearer's comfort, particularly in the foot area, while avoiding a need for modified or special footwear.

In an alternate embodiment of the present invention, the upper portion has a superior end having a width greater than the width of the elongated member. At least a portion of the inner surface of the device may be padded for additional comfort. The securing member may include or be composed of a strap attached to the exterior surface of the superior end. The securing member may then be wrapped or extend around the lower leg to secure the upper portion to the lower leg.

In another embodiment of the present invention, the device includes an elongated member the length of which is variable. The elongated member has an upper portion, an intermediate portion and a lower portion. The upper portion is positionable relative to the intermediate portion, the upper portion further adapted to extend along a superior anterior portion of the lower leg. The lower portion generally conforms to the dorsal surface of the foot and is adapted to engage an upper outer region of the footwear. The device further includes suitable structure for securing the lower portion to the upper region of the footwear, suitable structure for securing the upper portion to the intermediate portion, and a securing member. The lower portion is secured to the upper region of the footwear and the securing member secures the upper portion to the lower leg maintaining the person's foot in a dorsiflexion position as previously described. This embodiment thereby provides a selectively adjustable elongated member suitable to accommodate lower legs of different length. This avoids the need for multiple sizes of orthotic devices to accommodate individuals of different size.

The structure for securing the upper portion to the intermediate portion may be any suitable structure, such as, for example, one or more threaded fasteners such as a bolt or stud and a nut arrangement or other fasteners, snaps, straps, hook and loop fastening material, clamps and combinations thereof, with bolts and nuts preferred fasteners. In one embodiment, the upper portion, the intermediate portion, or both portions include at least one opening. A bolt inserted through the opening may be secured on a corresponding nut to secure the upper portion to the intermediate portion. In one embodiment, either the upper portion or the intermediate portion has at least one longitudinally elongated slot or opening or a plurality of longitudinally spaced apart openings and the other portion has at least one opening or stud. Preferably, the openings or opening and stud are alignable in an overlapping manner allowing a bolt stud or other fastener to be inserted through the opening or openings and fastened with a nut thereby securing the upper portion to the intermediate portion to provide a desired length. Preferably, the plurality of openings extends longitudinally in a spaced apart manner along either the upper portion or the intermediate portion or both portions. At least one opening may include an elongated slot extending longitudinally along the upper portion, the intermediate portion or both portions. At least one bolt or other fastener may then be inserted through the elongated slot and fastened with a nut to secure the upper portion to the intermediate portion.

In accordance with another aspect of the invention, a method is provided for preventing foot drop of a foot of a person wearing footwear with an ankle-foot orthotic device. The method includes applying the orthotic device to the lower leg and foot of the person. The orthotic device includes an elongated member having an upper portion, an intermediate portion and a lower portion. The upper portion is adapted to extend along an anterior portion of the lower leg below the person's knee. The intermediate portion transitions or extends between the upper portion and the lower portion and can be considered as part of the lower and/or upper portions. The lower portion generally conforms to a portion of the dorsal surface of the foot and is adapted to engage an upper outer region of the footwear. The method further includes securing the lower portion to an upper region of the footwear and securing the upper portion to the lower leg. Typically, the lower portion is secured to the footwear while the person's foot associated with the footwear is in a dorsiflexion position so that the upper region of footwear to which the lower portion is secured does not move relative to the lower portion. Preferably, the upper portion is selectively positionable relative to the intermediate portion. The method may further include attaching the upper portion to the intermediate portion and adjusting the position of the upper portion relative to the intermediate portion to accommodate the length of the person's lower leg.

BRIEF DESCRIPTION OF THE DRAWINGS

FIG. 1 is a front perspective view, partially in section, of the ankle-foot orthotic device in accordance with the present invention;

FIG. 2 is a front perspective view of the device of FIG. 1 applied to the leg and foot of a person;

FIG. 3 is a sectional view taken along line 3—3 of FIG. 2;

FIG. 4 is a front perspective view of an alternate embodiment of the present invention;

FIG. 5 is a sectional view taken along line 5—5 of FIG. 4;

FIG. 6 is a side elevation view of the present invention as worn by a person during the gait cycle;

FIG. 7 is a front perspective view of an alternate embodiment of the ankle-foot orthotic device in accordance with the present invention; and FIG. 8 is an exploded perspective view of the device of FIG. 7.

DETAILED DESCRIPTION OF THE PREFERRED EMBODIMENT

Referring to the FIGURES generally, where like reference numerals denote like structure and elements, and in particular to FIG. 1 which depicts an ankle-foot orthotic device 10 in accordance with the present invention having an elongated member 12 which includes an upper portion 14, an intermediate portion 16 and a lower portion 18. Elongated member 12 is generally L-shaped and adapted to extend along the lower leg and foot of a person with upper portion 14 conforming to an anterior portion of the lower leg, lower portion 18 conforming to a dorsal portion of the foot and intermediate portion 16 extending or bridging between upper portion 14 and lower portion 18. Intermediate portion 16 can be considered as part of upper portion 14 and/or lower portion 18. If desired, extending longitudinally along a generally central region of elongated member 12 a reinforcing rib 19 may be provided which increases the rigidity of elongated member 12. The contour of reinforcing rib 19 further promotes a comfortable fit with the anterior portion of the lower leg. Elongated member 12 is preferably made of a lightweight, rigid material with upper portion 14, intermediate portion 16 and lower portion 18 integral to each other. Nonlimiting examples of materials suitable for elongated member 12 include wood, carbon-fibre composites, rubber, polymer material, or metal. A lightweight polymer material, such as polypropylene, is preferred. Ankle foot orthotic device 10 may be very lightweight, on the order of about 3 ounces, for example.

Elongated member 12 may be configured as desired to fit various leg and foot sizes. For example, lower portion 18 may be formed to fit feet of various sizes and upper portion 14 may be formed to fit lower legs of various sizes. Typically, upper portion 14 does not extend above a person's knee. Preferably, elongated member 12 has a single size to accommodate foot and leg sizes of most patients. In this one-size-fits-all or most patients embodiment of device 10, elongated member 12 typically has a length between about 12 inches to about 20 inches and a width between about 1 inch to about 3 inches.

Elongated member 12 has an interior surface 20 that may be lined with padding 22. Padding 22 may extend along any desired portion of interior surface 20 or along the entire extent of interior surface 20 as shown in FIG. 1. Preferably padding 22 is a moisture resistant closed-cell foam that maintains resilience during periods of prolonged wear.

Upper portion 14 has a superior end 24 having flanges 26*a* and 26*b* which provide superior end 24 with a width greater than the width of elongated member 12. Flanges 26*a* and 26*b* are adapted to conform to the medial and lateral sides of a person's lower leg as shown in FIGS. 1 and 2. Flanges 26*a* and 26b may be made of a flexible material. Preferably, flanges 26a and 26b are integral to superior end 24.

Device 10 further includes a suitable securing member for securing upper portion 14 to the lower leg of a person. Any suitable securing member or structure known in the art can be utilized. Preferably, a securing member 32 is composed of a strap which extends along superior end 24, flanges 26a and 26b and encircle or extends around a person's lower leg 34 as shown in FIG. 2. Securing member 32 may be made of a flexible, expandable or otherwise stretchable material such as elastic or the like with an outer surface having hook and loop fastening material 36a such as Velcro®. This enables an overlapping end 38 of securing member 32 to attach to securing member 32 as shown in FIG. 2. Alternatively, securing member 32 may include a buckle to adjust the length of securing member 32 as desired. Preferably, exterior surface 39 of superior end 24 has hook or loop fastening material 36b attached thereto as shown in FIG. 1. Consequently, attaching hook or loop fastening material 36a and 36b together securely affixes securing member 32 to superior end 24. It is understood that securing member 32 may directly contact the lower leg or securing member 32 may wrap around the lower leg of a person wearing trousers, slacks, pants or the like.

Lower portion 18 conforms to the dorsal portion of the foot and is adapted to engage an upper outer region of footwear 40 as shown in FIG. 2. The term "footwear" is intended to encompass any covering commonly worn on the feet having an upper portion that covers a region of the dorsal surface of the foot. Nonlimiting examples of footwear in accordance with the present invention include shoes and boots extending either above or below the ankle with or without laces, athletic shoes, slippers, galoshes, sandals, loafers, flats, pumps, and skates. In FIGS. 2–6, footwear 40 is a shoe having a sole 42, an upper sole portion 44, eyelets 46, upper tabs 48a and 48b, a tongue 50 and laces 52. Lower portion 18 may include openings 54a and 54b. One of ordinary skill in the art will recognize that the number of openings may range from one to as many as about ten.

In one embodiment of the present invention, lower portion 18 is placed on an upper outer region of footwear 40 as seen in FIGS. 2 and 3. In this embodiment, padding 22 on interior surface 20 of lower portion 18 engages the outer surfaces of upper tabs 48a and 48b. Laces 52 are inserted through openings 54a and 54b in any manner as is commonly known in the art with a crossing lace arrangement being preferred. Tying laces 52 thereby secures lower portion 18 to footwear 40 while simultaneously securing footwear 40 to the person's foot.

In an alternate embodiment of the present invention, lower portion 18 is inserted between tongue 50 and upper tabs 48a and 48b so that padding 22 of interior surface 20 of lower portion 18 engages tongue 50 as shown in FIGS. 4 and 5. A portion of reinforcing rib 19 and portions of openings 54a and 54b extend above upper tabs 48a and 48b allowing laces 52 to be inserted into openings 54a and 54b. Laces 52 may then be arranged and tied to secure lower portion 18 to footwear 40 as previously described. The skilled artisan will understand that lower portion 18 may be adapted so that straps or other similar footwear securing devices that are generally wider and thicker than laces may be inserted through openings 54a and 54b.

Also within the scope of the present invention is lower portion 18 having no openings and adapted to engage footwear having no laces and a cavity between the tongue or similar article and an upper footwear portion. Examples of such footwear may be socks, loafers, women's flats or pumps, or similar shoe types that slide on and off the foot as is commonly known in the art. With this type of footwear, lower portion 18 may be inserted between the tongue and upper portion of the footwear. Lower portion 18 may be formed to reduce the protrusion of reinforcing rib 19 and the width of lower portion 18 may be increased or decreased as necessary in order to properly fit into the cavity between the tongue and upper footwear portion. Once inserted into the cavity, lower portion 18 is affixed to the footwear through friction fit. Consequently, an advantage of device 10 is that lower portion 18 does not directly engage the dorsal surface of the person's foot. This avoids friction between device 10 and the wearer's foot reducing the possibility of skin irritation or tissue damage to the person wearing device 10, particularly during periods of prolonged wear and particularly for patients having insensate feet, or feet prone to swelling, ulceration or with diminished healing capacity.

A further advantage of the present invention is that device 10 maintains a person's foot in a dorsiflexion position throughout the entire gait cycle. Once secured to the lower leg and footwear, the rigidity of device 10 maintains the foot in a dorsiflexion position during heel strike 56, toe-off 58 and swing 60 (depicted in phantom and by arrow A) as shown in FIG. 6. Device 10 properly plants the foot at heel strike, avoiding foot slap. Device 10 also prevents foot drag and/or foot slap during toe-off 58 and during leg swing 60. During toe-off 58 (the point at which the toe leaves the ground during walking), device 10 stores a small amount of energy to help the patient push off as lower portion 18 may be flexed slightly downwardly if lower portion 18 is constructed for slight flexing during a person's gait. Device 10 promotes a balanced gait for the wearer of device 10. Consequently, secondary impediments resulting from foot drop such as overcompensation and stresses to other joints such as the ankle, knee and hip are reduced by application of device 10. In addition, device 10 is lightweight, easy to apply and remove, and can be worn discreetly under clothing.

In an alternate embodiment of the present invention, ankle-foot orthotic device 62 has an elongated member 64 that is variable in length as shown in FIG. 7. Elongated member 64 includes upper portion 66, intermediate portion 68 and lower portion 70. Upper portion 66 may be positioned along the length of intermediate portion 68 to vary the length of elongated member 64. Upper portion 66 is adapted to extend along a superior anterior portion of the lower leg. Intermediate portion 68 is adapted to extend along an inferior anterior portion of the lower leg. Intermediate portion 68 also extends between upper portion 66 and lower portion 70. Lower portion 70 generally conforms to a portion of the dorsal surface of the foot and is adapted to engage a person's footwear as previously described. Elongated member 64 has an inner surface 72 that may include a padding 74 as previously described.

Upper portion 66 has a superior end 76 wider than elongated member 64. Device 62 further includes a securing member 78 which may be affixed to superior end 76 as is commonly known in the art. A rivet 80 preferably affixes one end of securing member 78 to superior end 76. A buckle 82 allows the length of securing member 78 to be adjusted as is commonly known in the art. Buckle 82 includes a slot 84 corresponding to rivet 80. Inserting rivet 80 through slot 84 secures buckle 82 to superior end 76. Securing member 78 may be made of a stretchable material and hook and fastening material and secures upper portion 66 to the lower leg as previously described.

Upper portion 66 may be selectively positioned lengthwise along the length of intermediate portion 68 providing elongated member 64 with a variable length to accommodate lower legs of varying lengths. Any suitable structure as is commonly known in the art may be used to secure upper portion 66 to intermediate portion 68 including, but not limited to, nuts and bolts, snaps, rivets, straps, hook and loop fastening material and any combination thereof. Preferred is a bolt and nut arrangement as shown in FIGS. 7 and 8. Intermediate portion 68 may include a plurality of spaced apart openings 85a, 85b, 85c, 85d and 85e extending longitudinally along a generally central region of intermediate portion 68. Bolts 86a and 86b may be secured to an inferior portion of upper portion 66. Bolts 86a and 86b may then be inserted into any two corresponding openings 85a–85e to provide a desired length for elongated member 64. Nuts 88a and 88b corresponding to bolts 86a and 86b, respectively, secure upper portion 66 to intermediate portion 68. It is understood that a portion of upper portion 66 and a portion of intermediate portion 68 overlap for proper attachment to occur. Once elongated member 64 is adjusted to properly accommodate the length of the lower leg, device 62 is applied to the lower leg and lower portion 70 engages and secures to footwear as previously described. Lower portion 70 may include a plurality of openings 71a, 71b, and 71c used for securing lower portion 70 to the footwear as previously described.

The present invention contemplates various embodiments for attaching upper portion 66 to intermediate portion 68. In addition, one of ordinary skill in the art will recognize that the number of bolts and corresponding nuts may be varied as desired with the number of bolts (and corresponding nuts) preferably ranging from one to about four. Correspondingly, the number of openings may vary as desired. Preferably, the number of openings range from about one to about ten in number. It is understood that the openings may be disposed on either upper portion 66, or intermediate portion 68 or both upper portion 66 and intermediate portion 68. A plurality of openings may be disposed laterally across either upper portion 66 or intermediate portion 68 into which bolts are inserted and secured with nuts. Alternatively, the bolts may be secured to intermediate portion 68 and extend through openings in upper portion 66 or vice versa. In another embodiment, both upper and intermediate portions 66 and 68 may include openings through which bolts, screws or the like may be inserted.

In a further embodiment, either upper portion 66, or intermediate portion 68, or both upper portion 66 and intermediate portion 68 may be configured to include an elongated slot (not shown) extending longitudinally along a central region of either portion in place of holes 85a–e. Bolts affixed to the portion without the elongated slot may be inserted through the elongated slot and a nut having a width larger than the width of the elongated slot may be secured to the bolt thereby securing upper portion 66 to intermediate portion 68. Alternatively, both upper portion 66 and intermediate portion 68 may include a centrally disposed elongated slot (not shown). The slots may be aligned with each other in an overlapping manner and at least one bolt may be inserted through both slots. A nut having a width greater than the width of each slot may be used to secure upper portion 66 to intermediate portion 68.

In yet another embodiment, intermediate portion 68 and upper portion 66 may be configured to be held in sliding engagement (not shown) to each other with a plurality of longitudinally disposed openings to provide elongated member 64 with an adjustable length. Upper portion 66 may be configured to include at least one spring-actuated prong (not shown) that extends through at least one opening to rigidly secure upper portion 66 to intermediate portion 68. Alternately, one of ordinary skill in the art will recognize that intermediate portion 68 may be configured to be slideably attached to upper portion 66 having a plurality of longitudinally disposed openings. Intermediate portion 68 may be configured to include a spring-actuated prong that extends through at least one opening to rigidly secure intermediate portion 68 to upper portion 66. Upper portion 66 may also be configured to be slideably attached to intermediate portion 68 in a telescoping manner yielding an elongated member variable in length. One skilled in the art will further appreciate that lower portion 70 may be configured to be positionable and selectively adjustable relative to intermediate portion 68 in a manner as described in any of the previous embodiments.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

The invention claimed is:

1. A device securable to a leg of a person wearing footwear to prevent foot drop with respect to the leg comprising:
   an elongated member having an upper portion, an intermediate portion and a lower portion, the upper portion adapted to extend along an anterior portion of the lower leg below the person's knee, the intermediate portion extending between the upper portion and the lower portion, the lower portion generally conforming to a portion of the dorsal surface of the foot and adapted to be secured to an upper outer region of the footwear;
   means for securing the lower portion to an upper region of the footwear; and
   a securing member for securing the upper portion to the lower leg, the device maintaining the person's foot in a dorsiflexion position when worn by the person.

2. The device of claim 1 wherein the means for securing the lower portion to the upper region of the footwear comprises at least one opening.

3. The device of claim 1 wherein a reinforcing rib extends longitudinally along a generally central region of the intermediate portion.

4. The device of claim 1 wherein the elongated member has an inner surface and the device further comprises padding covering at least a portion of the inner surface.

5. The device of claim 1 wherein the elongated member has a superior end, the superior end having a width greater than the elongated member.

6. A device securable to a leg of a person wearing footwear to prevent foot drop with respect to the leg comprising:
   an elongated member having an upper portion, an intermediate portion and a lower portion, the upper portion adapted to extend along an anterior portion of the lower leg below the person's knee, the intermediate portion extending between the upper portion and the lower portion, the lower portion generally conforming to a portion of the dorsal surface of the foot and adapted to engage an upper outer region of the footwear;
   means for securing the lower portion to an upper region of the footwear; and a securing member for securing the upper portion to the lower leg, the device maintaining the person's foot in a dorsiflexion position when worn by the person, wherein the means for securing the lower portion to the upper region of the footwear comprises at least one opening, and wherein the opening is disposed in and extends through the lower portion in a location such that when worn by a person permits a shoelace of the footwear to pass through the opening and secure the lower portion to the upper region of the footwear.

7. The device of 6 wherein the lower portion is adapted to fit between an upper tab and a tongue of the footwear.

8. A device securable to a leg of a person wearing footwear to prevent foot drop with respect to the leg comprising:

an elongated member of variable length, the elongated member having an upper portion, an intermediate portion and a lower portion, the upper portion positionable along the intermediate portion to vary the length of the elongated member, the upper portion adapted to extend along a superior anterior portion of the lower leg, the intermediate portion adapted to extend along an inferior anterior portion of the lower leg and extending between the upper portion and lower portion, the lower portion generally conforming to a portion of the dorsal surface of the foot and adapted to secure an upper outer region of the footwear;

means for securing the lower portion to the upper region of the footwear;

means for securing the upper portion to the intermediate portion; and a securing member for securing the elongated member to the lower leg below the person's knee, the device maintaining the person's foot in a dorsiflexion position when worn by the person.

9. The device of claim 8 wherein the length of the device is selectively adjustable to accommodate lower legs of different length.

10. The device of claim 8 wherein the means for securing the upper portion to the intermediate portion is selected from the group consisting of threaded fasteners, snaps, straps, hook and loop fastening material and combinations thereof.

11. The device of claim 8 wherein at least a portion of the upper portion and at least a portion of the intermediate portion overlap.

12. The device of claim 8 wherein the upper portion is slideably moveable relative to the intermediate portion.

13. The device of claim 8 wherein the intermediate portion has a first opening and the upper portion has a second opening corresponding to the first opening.

14. The device of claim 13 wherein said means for securing the upper portion to the intermediate portion is insertable through said first and second openings.

* * * * *